US007799072B2

(12) United States Patent
Greenberg

(10) Patent No.: US 7,799,072 B2
(45) Date of Patent: Sep. 21, 2010

(54) APPARATUS AND METHODS FOR REPAIRING THE FUNCTION OF A DISEASED VALVE AND METHOD FOR MAKING SAME

(75) Inventor: Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 195 days.

(21) Appl. No.: 11/436,521

(22) Filed: May 18, 2006

(65) Prior Publication Data
US 2006/0276813 A1 Dec. 7, 2006

Related U.S. Application Data

(60) Provisional application No. 60/682,939, filed on May 20, 2005.

(51) Int. Cl.
*A61F 2/24* (2006.01)
(52) U.S. Cl. .................................................. 623/2.14
(58) Field of Classification Search ............. 623/1.13, 623/1.26, 2.1
See application file for complete search history.

(56) References Cited

U.S. PATENT DOCUMENTS

| 5,178,634 | A | | 1/1993 | Ramos Martinez |
| 5,314,468 | A | | 5/1994 | Ramos Martinez |
| 5,843,158 | A | * | 12/1998 | Lenker et al. ............... 623/1.13 |
| 5,957,949 | A | | 9/1999 | Leonhardt et al. |
| 6,001,126 | A | * | 12/1999 | Nguyen-Thien-Nhon .. 623/2.11 |
| 6,517,570 | B1 | * | 2/2003 | Lau et al. .................... 623/1.13 |
| 6,682,476 | B2 | * | 1/2004 | Alferness et al. .............. 600/37 |
| 7,377,938 | B2 | * | 5/2008 | Sarac et al. ................. 623/1.26 |
| 7,442,204 | B2 | * | 10/2008 | Schwammenthal et al. 623/1.24 |
| 2001/0000188 | A1 | * | 4/2001 | Lenker et al. ............... 623/1.13 |
| 2002/0032481 | A1 | * | 3/2002 | Gabbay ...................... 623/2.11 |
| 2002/0156523 | A1 | * | 10/2002 | Lau et al. .................... 623/1.13 |
| 2002/0193871 | A1 | | 12/2002 | Beyersdorf et al. |
| 2003/0023300 | A1 | * | 1/2003 | Bailey et al. ................ 623/1.13 |
| 2003/0023303 | A1 | | 1/2003 | Palmaz et al. |
| 2003/0040792 | A1 | * | 2/2003 | Gabbay ...................... 623/2.11 |
| 2003/0130611 | A1 | * | 7/2003 | Martin ........................... 604/8 |
| 2003/0130730 | A1 | * | 7/2003 | Cohn et al. ................. 623/2.36 |

(Continued)

FOREIGN PATENT DOCUMENTS

WO WO 2004/034933 A2 4/2004

(Continued)

*Primary Examiner*—David Isabella
*Assistant Examiner*—Jonathan Stroud
(74) *Attorney, Agent, or Firm*—Tarolli, Sundheim, Covell & Tummino LLP

(57) ABSTRACT

An apparatus for repairing the function of a diseased valve includes an annular first support member expandable to a first diameter. An annular second support member is spaced axially apart from the first support member and is expandable to a second diameter that is independent of the first diameter. A tubular graft section interconnects the first and second support members. The graft section defines an annulus having a third diameter that is independent of each of the first and second diameters. A prosthetic valve is secured within the annulus of the graft section. The bioprosthetic valve has at least two valve leaflets that are coaptable to permit the unidirectional flow of blood. Methods for repairing the function of a diseased valve and for making the apparatus are also provided.

10 Claims, 13 Drawing Sheets

U.S. PATENT DOCUMENTS

| | | | |
|---|---|---|---|
| 2004/0054396 A1* | 3/2004 | Hartley et al. | 623/1.13 |
| 2004/0093070 A1* | 5/2004 | Hojeibane et al. | 623/1.15 |
| 2004/0106976 A1* | 6/2004 | Bailey et al. | 623/1.11 |
| 2004/0167606 A1* | 8/2004 | Chouinard | 623/1.13 |
| 2004/0236411 A1 | 11/2004 | Sarac et al. | |
| 2004/0260389 A1* | 12/2004 | Case et al. | 623/1.24 |
| 2005/0043785 A1* | 2/2005 | Tanner et al. | 623/1.36 |
| 2005/0043790 A1 | 2/2005 | Seguin | |
| 2005/0055082 A1* | 3/2005 | Ben Muvhar et al. | 623/1.15 |
| 2005/0060026 A1* | 3/2005 | Gamboa | 623/1.35 |
| 2005/0075725 A1* | 4/2005 | Rowe | 623/2.14 |
| 2005/0085893 A1* | 4/2005 | Roy | 623/1.13 |
| 2005/0096736 A1* | 5/2005 | Osse et al. | 623/1.26 |
| 2005/0222674 A1* | 10/2005 | Paine | 623/1.24 |
| 2007/0142906 A1* | 6/2007 | Figulla et al. | 623/2.11 |
| 2007/0156233 A1* | 7/2007 | Kapadia et al. | 623/2.11 |
| 2007/0239269 A1* | 10/2007 | Dolan et al. | 623/2.11 |
| 2007/0250154 A1* | 10/2007 | Greenberg et al. | 623/1.13 |

FOREIGN PATENT DOCUMENTS

| | | |
|---|---|---|
| WO | WO 2004/034933 A3 | 4/2004 |
| WO | WO 2004/093935 A2 | 11/2004 |

* cited by examiner

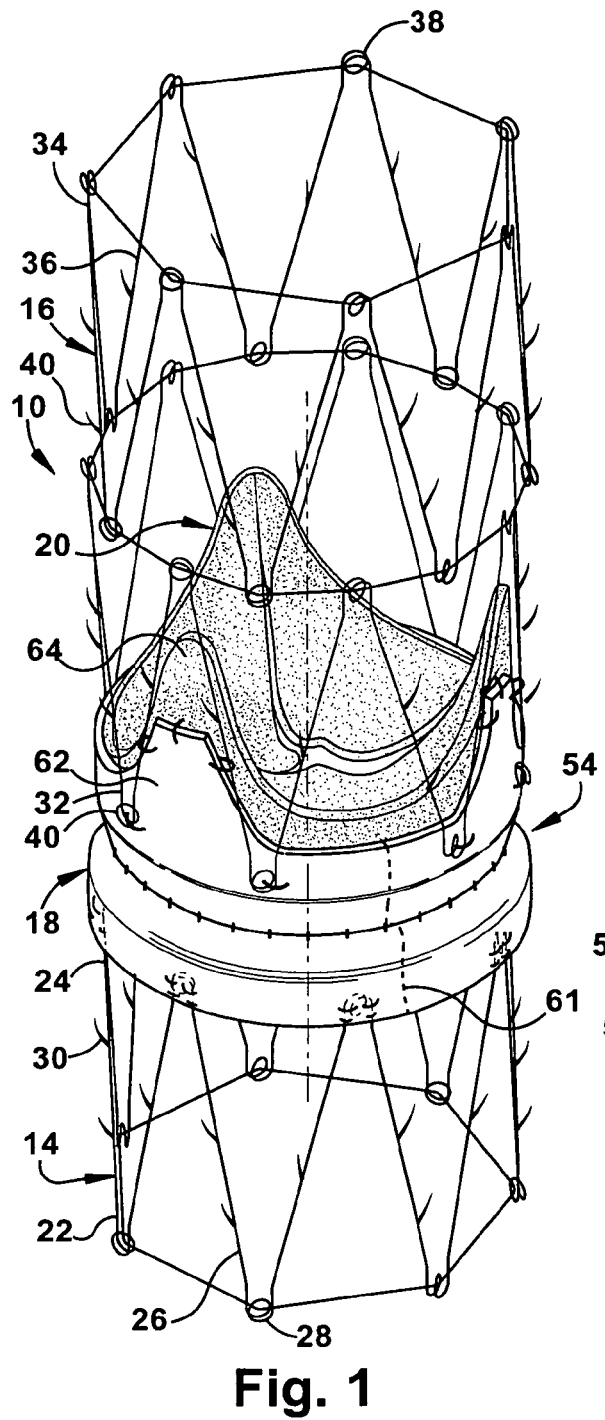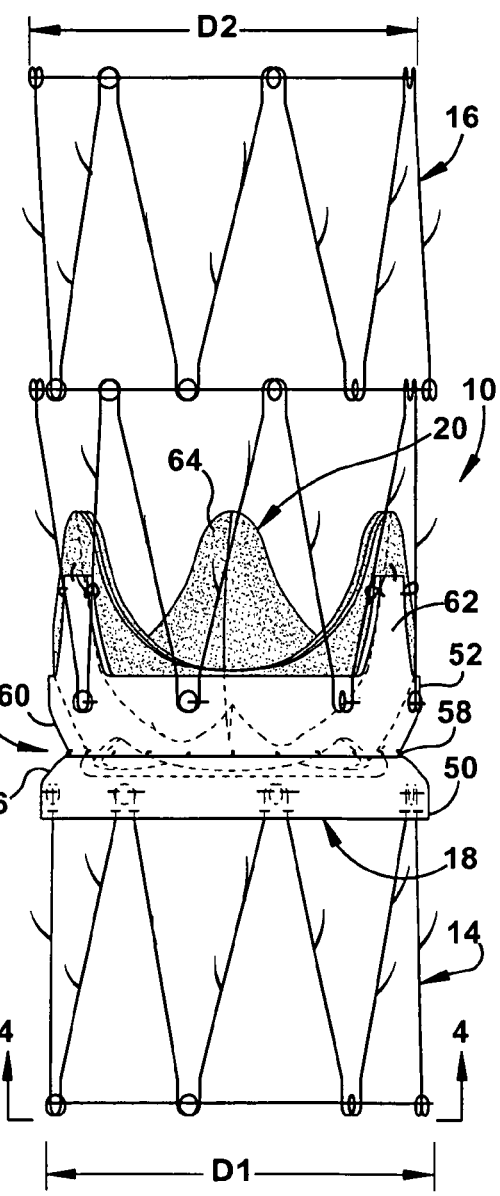
Fig. 1
Fig. 2

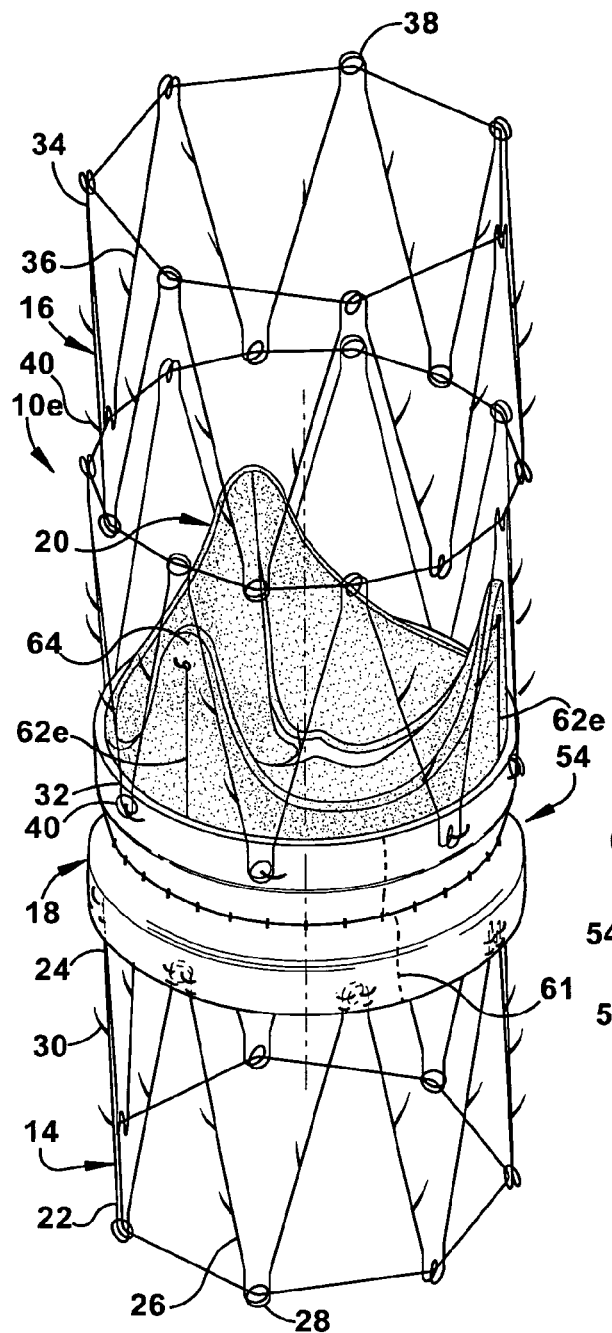
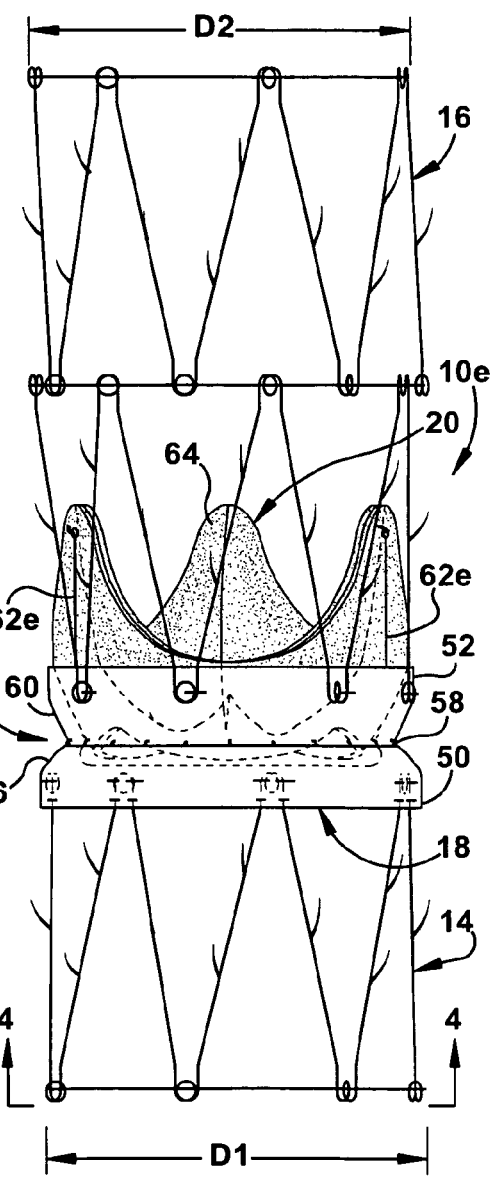
Fig. 16
Fig. 17

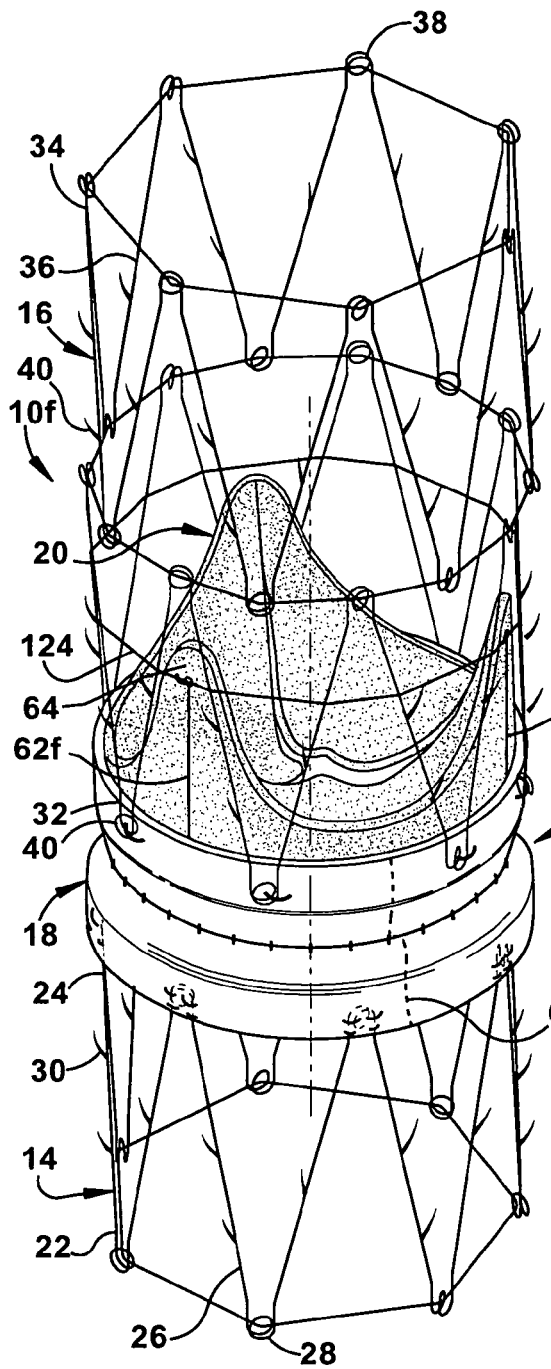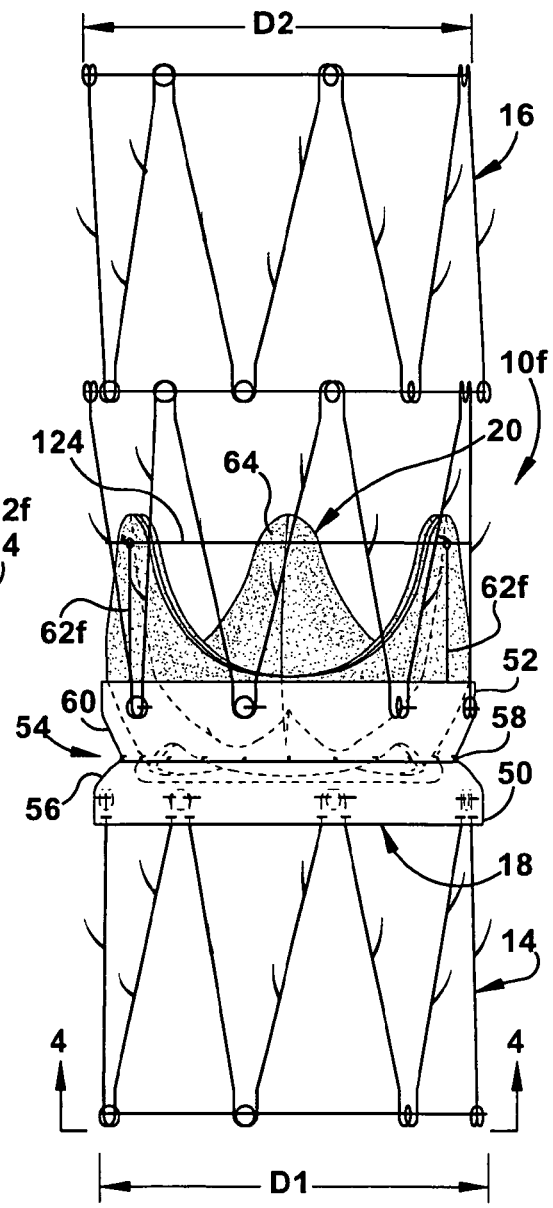
Fig. 18
Fig. 19

APPARATUS AND METHODS FOR REPAIRING THE FUNCTION OF A DISEASED VALVE AND METHOD FOR MAKING SAME

RELATED APPLICATION

This application claims the benefit of U.S. Provisional Patent Application Ser. No. 60/682,939, filed on May 20, 2005, the subject matter of which is incorporated herein by reference.

FIELD OF THE INVENTION

The present invention is directed to an apparatus and methods for repairing the function of a diseased valve, such as a cardiac or venous valve, via an endovascular technique, and is further directed to methods for making the apparatus.

BACKGROUND OF THE INVENTION

It is known to implant prosthetic valves in various body passages to replace native valves that are diseased or otherwise defective in some manner. Blood pressure, as provided by heart activity via the arteries, is normally sufficient to maintain the flow of blood in one direction through the vasculature. The blood pressure in the veins is much lower than in the arteries and venous valves function to limit the backflow of blood through the veins. Numerous such venous valves are located throughout the venous system and are particularly important to maintaining directional blood flow in the lower extremities.

Venous valves can become incompetent and lead to chronic venous insufficiency. Various surgical techniques have been developed for treating incompetent venous valves including valvuloplasty, transplantation, and replacement with a prosthetic valve. These known surgical techniques include both open and percutaneous approaches. As with any prosthetic, compatibility issues for prosthetic venous valves are important, along with the need to avoid thrombosis and platelet deposition.

Another common type of prosthetic valve is a prosthetic cardiac valve. Prosthetic cardiac valves have been used to replace all four of the native cardiac valves. Cardiac valve replacement has traditionally been done though an invasive open surgical procedure, although endovascular (or percutaneous) approaches are being developed.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native cardiac valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Cardiac valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with cardiac valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of cardiac valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a cardiac valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves.

Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark DACRON™, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not necessarily require systemic anticoagulation.

Homograft valves are harvested from human cadavers. Homograft valves are most commonly implanted in the aortic position, but are also occasionally implanted in the pulmonary position. Homograft valves are specially prepared and frozen in liquid nitrogen, where they are stored for later use. The advantage of aortic homograft valves is that they appear to be as durable as mechanical valves, but do not promote blood clot formation and therefore do not require anticoagulation. The main disadvantage of these valves is that they are not available in sufficient numbers to satisfy the needs of patients who need new aortic or pulmonary valves. Homograft valves are also extremely expensive and can be more difficult to implant than either mechanical valves or tissue valves.

Cardiac valve replacement using any of the aforementioned prostheses has traditionally been done via an open surgical technique in which the thoracic cavity is opened. This exacting operation requires use of a heart-lung machine for external circulation of the blood as the heart is stopped and opened during the surgical intervention and the artificial cardiac valve is implanted under direct vision. This operation exposes the patient to many risks especially in the elderly population. Hence, an apparatus for repairing the function of a diseased cardiac or venous valve via an endovascular (or percutaneous) procedure, rather than an open surgical procedure, could offer tremendous benefits for these patients, many of whom have no options today.

SUMMARY OF THE INVENTION

The present invention includes an apparatus for repairing the function of a diseased valve. The apparatus comprises an annular first support member expandable to a first diameter. An annular second support member is spaced axially apart from the first support member and is expandable to a second diameter that is independent of the first diameter. A tubular graft section interconnects the first and second support members. The graft section defines an annulus having a third diameter that is independent of each of the first and second diameters. A prosthetic valve is secured within the annulus of the graft section. The bioprosthetic valve has at least two valve leaflets that are coaptable to permit the unidirectional flow of blood.

In accordance with one aspect of the invention, an expandable ring encircles the annulus of the graft section and supports the prosthetic valve secured within the annulus.

In accordance with another aspect of the invention, the apparatus further comprises at least one tubular conduit having first and second ends. The second end is received in a passage in the graft section and the first end is for positioning in a branch blood vessel.

In accordance with another aspect of the invention, a method for making an apparatus to repair the function of a diseased valve is provided. According to the inventive method an annular first support member expandable to a first diameter and an annular second support member expandable to a second diameter that is independent of the first diameter are provided. A tubular graft section is also provided. The graft section defines an annulus having a third diameter that is independent of each of the first and second diameters. The first and second support members are interconnected with the graft section such that the support members are spaced axially apart by the graft section. A bioprosthetic valve having at least two valve leaflets that are coaptable to permit the unidirectional flow of blood is secured within the annulus of the graft section.

In accordance with another aspect of the invention, a minimally invasive method for repairing the function of a diseased valve is provided. According to the inventive method, an apparatus including annular first and second support members that are spaced axially apart and are expandable to independent first and second diameters, respectively, is provided. The apparatus further includes a prosthetic valve and a tubular graft section interconnecting the first and second support members. The graft section defines an annulus having a third diameter that is independent of the first and second diameters. The prosthetic valve is secured within the annulus of the graft section. The apparatus is collapsed and loaded into a sheath for intravascular delivery. The apparatus is inserted into the vasculature and advanced to a location with the vasculature adjacent the diseased valve. The sheath is retracted and the first and second support members expand into engagement with the vasculature at the respective first and second diameters to form a seal between at least one of the first and second support members and the vasculature. The suspension of the prosthetic valve inside the graft section at the third diameter and within the vasculature adjacent the diseased valve assumes the function of the diseased valve.

In accordance with another aspect of the present invention, an apparatus for repairing the function of a diseased valve comprises an annular support member having inner and outer surfaces. The support member is expandable to a first diameter. A tubular first graft section for sealing against a vessel wall adjacent the diseased valve is connected to the outer surface of the support member. A tubular second graft section is secured to the inner surface of the support member. The second graft section defines an annulus having a second diameter that is smaller than and independent of the first diameter of the support member. A prosthetic valve is secured within the annulus of the second graft section. The bioprosthetic valve has at least two valve leaflets that are coaptable to permit the unidirectional flow of blood.

In accordance with another aspect of the present invention, a method for making an apparatus to repair the function of a diseased valve is provided. According to the inventive method, an annular support member expandable to a first diameter is provided. The support member has inner and outer surfaces. A tubular first graft section is connected to the outer surface of the support member for sealing against a vessel wall adjacent the diseased valve. A tubular second graft section is connected to the inner surface of the support member. The second graft section defines an annulus having a second diameter that is smaller than and independent of the first diameter. A bioprosthetic valve having at least two valve leaflets that are coaptable to permit the unidirectional flow of blood is secured within the annulus of the second graft section.

In accordance with another aspect of the present invention, a minimally invasive method for repairing the function of a diseased valve is provided. According to the inventive method, an apparatus including an annular support member having inner and outer surfaces and which is expandable to a first diameter is provided. The apparatus further includes a prosthetic valve and first and second tubular graft sections. The first graft section is connected to the outer surface and the second graft section is connected to the outer surface. The second graft section defines an annulus having a second diameter that is smaller than and independent of the first diameter. The prosthetic valve is secured within the annulus of the second graft section. The apparatus is collapsed and loaded into a sheath for intravascular delivery. The apparatus is inserted into the vasculature and advanced to a location with the vasculature adjacent the diseased valve. The sheath is retracted and the support member is expanded into engagement with the vasculature, forming a seal between the first graft section and the vasculature. The suspension of the prosthetic valve inside the second graft section at the second diameter and within the vasculature adjacent the diseased valve assumes the function of the diseased valve.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic perspective view of an apparatus for repairing the function of a diseased valve in accordance with the present invention;

FIG. 2 is a schematic side view of the apparatus of FIG. 1;

FIG. 16 is a schematic perspective view of an apparatus for repairing the function of a diseased valve in accordance with a fifth embodiment of the present invention;

FIG. 17 is a schematic side view of the apparatus of FIG. 16;

FIG. 18 is a schematic perspective view of an apparatus for repairing the function of a diseased valve in accordance with a sixth embodiment of the present invention;

FIG. 19 is a schematic side view of the apparatus of FIG. 18;

DETAILED DESCRIPTION OF EMBODIMENTS

Figure 3:
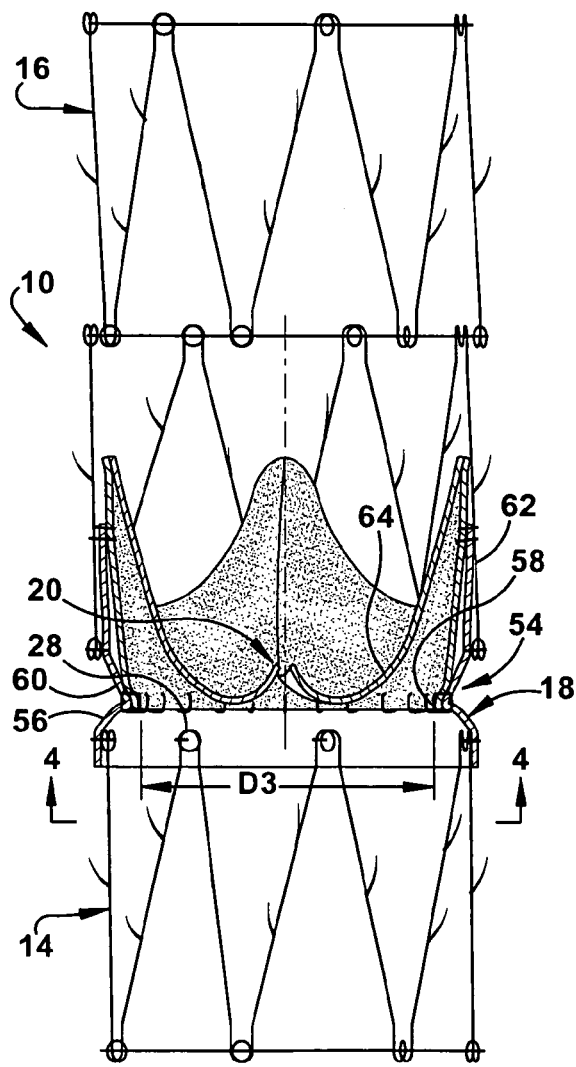
FIG. 3 is a schematic sectional view of the apparatus of FIG. 1.

The present invention is directed to an apparatus and methods for repairing the function of a diseased valve, such as a cardiac or venous valve, via an endovascular technique, and is further directed to methods for making the apparatus. As representative of the present invention, FIGS. 1-4 illustrate a first embodiment of an apparatus 10 for repairing the function of a diseased cardiac valve, such as a tricuspid valve 12 shown schematically in FIGS. 6-8. It should be apparent, however, to those skilled in the art that the apparatus 10 disclosed herein can also be used to repair the function of other cardiac valves as well as venous valves. The apparatus 10 includes annular first and second support members 14 and 16, a tubular graft section 18 interconnecting the support members, and a prosthetic valve 20 secured within the graft section.

The first support member 14 comprises a self-expanding or balloon expandable stent made from stainless steel, but could alternatively be made from any suitable medical grade plastic or metal, including shape memory metals such as Nitinol. The first support member 14 has oppositely disposed proximal and distal ends 22 and 24 connected by axially extending beams 26 having a known "M" or "Z" shape.

The axially extending beams 26 define generally cylindrical inner and outer surfaces (not numbered) for the first support member 14. In the expanded condition shown in FIGS. 1-4, the outer surface of the first support member 14 has a first diameter D1 (FIG. 2) that has been selected to exceed the largest potential venous diameter for a given patient.

Both the proximal and distal ends 22 and 24 of the first support member 14 include a plurality of eyelets 28 spaced circumferentially about the ends. The first support member further includes a plurality of hooks (or barbs) 30 located on the outer surface of the beams 26. The hooks 30 extend radially outward and at an angle to prevent migration of the support member 14 upon implantation. It should be understood that the location, quantity, configuration, and orientation of the hooks 30 may be altered depending on specific needs of the apparatus 10.

The second support member 16 resembles the first support member 14 and comprises two conjoined self-expanding stents made from stainless steel, but which could alternatively be made from any suitable medical grade plastic or metal, including shape memory metals such as Nitinol. The two stents of the second support member 16 together define oppositely disposed proximal and distal ends 32 and 34 connected by axially extending beams 36 having a known "M" or "Z" shape.

The axially extending beams 36 define generally cylindrical inner and outer surfaces (not numbered) for the second support member 16. In the expanded condition shown in FIGS. 1-4, the outer surface of the second support member 16 has a second diameter D2 that has been selected to exceed the largest potential venous diameter for a given patient. It should be noted that, when implanted, the second support member 16 is free to expand to the second diameter D2 (FIG. 2) independent of the expansion of the first support member 14 to the first diameter D1.

Both the proximal and distal ends 32 and 34 include a plurality of eyelets 38 spaced circumferentially about the ends. The second support member further includes a plurality of hooks (or barbs) 40 located on the outer surface of the beams 36. The hooks 40 extend radially outward and at an angle to prevent migration of the support member upon implantation. It should be understood that the location, quantity, and configuration of the hooks 40 may be altered depending on the specific needs of the apparatus 10.

It should also be understood that that the invention is not limited to the particular configuration of the illustrated first and second support members 14 and 16, and that the first and second support members need not be similarly configured. Further, it is contemplated that the lengths of the first and second support members 14 and 16 will be varied based on the needs of a particular implantation. In addition, it should be noted that radiopaque markers may be attached at various locations on the first and second support members 14 and 16 to aid with placement of the apparatus 10 under fluoroscopy.

To enhance the biocompatibility of the apparatus 10, it is contemplated that at least a portion of the first and second support members 14 and 16 may be coated with a therapeutic agent such as, for example, an anti-coagulant, an anti-thrombogenic agent, an anti-proliferative agent, an anti-inflammatory agent, an antibiotic, an angiogenesis agent, a statin, a growth factor, or stem cells. The therapeutic agent may be loaded into a compound or polymer that is coated onto the support members 14 and 16 for a time-delayed release into surrounding tissue.

The apparatus 10 further includes the tubular graft section 18 interconnecting the first and second support members 14 and 16. The graft section 18 comprises a biocompatible material such as Dacron®, woven velour, polyurethane, PTFE, or heparin-coated fabric. Alternatively, the graft section 18 may be a biological material such as bovine or equine pericardium, a homograft, an autograft, or cell-seeded tissue.

The graft section 18 has an hourglass shape defined by first and second end portions 50 and 52 (FIG. 2) and a neck portion 54 located between the ends. The neck portion 54 of the graft section 18 is formed by a converging portion 56, which extends inward from the first end 50 to an annulus 58, and a diverging portion 60, which extends outward from the annulus toward the second end 52. The annulus 58 of the graft section 18 defines a third diameter D3 that is less than and independent of the first and second diameters D1 and D2 of the first and second support members 14 and 16, respectively. As may be seen in FIG. 1, one or more axial seams 61 in the graft section 18 are used to create a smaller diameter at the annulus 58 than at either of the end portions 50 and 52.

The first end portion 50 of the graft section 18 is secured about the outer surface of the distal end 24 of the first support member 14. As shown in FIGS. 1-4, the first end portion 50 may be sutured to the eyelets 28 at the distal end 24 of the first support member 14. Alternatively, it is contemplated that first end portion 50 may be sutured to other structure at the distal end 24 of the first support member 14 depending on the configuration of the stent used. It is further contemplated that the first end portion 50 may be woven to the distal end 24 of the first support member 14 or otherwise attached in another suitable manner.

The second end portion 52 of the graft section 18 is secured to the inner surface of the proximal end 32 of the second support member 16. As shown in FIGS. 1-4, the second end portion 52 may be sutured to the eyelets 38 at the proximal end 32 of the second support member 16. Alternatively, it is contemplated that the second end portion 52 may be woven to the proximal end 32 of the second support member 16 or otherwise attached in another suitable manner.

The second end portion 52 of the graft section 18 further includes a plurality of extension flaps 62 that extend axially toward the distal end 34 of the second support member 16. The extension flaps 62 are connected, such as by sutures, to the beams 36 of the second support member 16. The number and circumferential orientation of the extension flaps 62 correspond to the number and orientation of leaflets in the prosthetic valve 20.

The bioprosthetic valve 20 may be a homograft, an autograft, or made from a harvested biological material including, but not limited to, bovine pericardial tissue, equine pericardial tissue or porcine pericardial tissue. Alternatively, the bioprosthetic valve 20 may be made from a biocompatible synthetic material including, but not limited to, polyurethane or expanded PTFE.

The bioprosthetic valve 20 is secured, by sutures or other suitable means, within the annulus 58 of the neck portion 54 of the graft section 18 so that the valve is suspended inside the graft section at the third diameter D3. In the illustrated embodiments, the bioprosthetic valve 20 has three leaflets 64 that are coaptable to permit the unidirectional flow of blood. However, it should be understood that the prosthetic valve 20 could have less than three or more than three leaflets. Each of the leaflets 64 of the prosthetic valve 20 may be sutured to a respective one of the extension flaps 62 of the graft section 18 to create a minor amount of valve insufficiency in the apparatus 10 if so desired.

Figure 5:
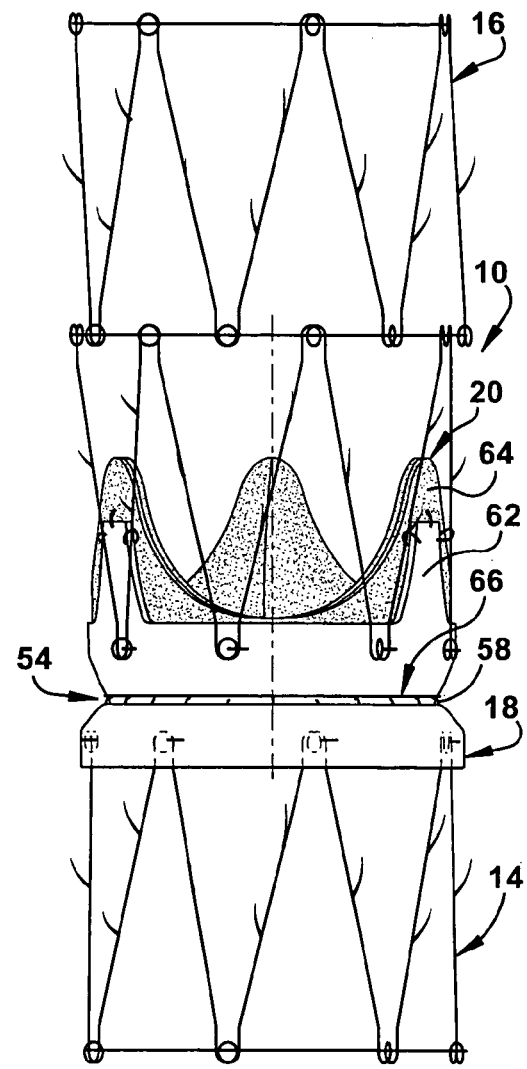
FIG. 5 is a side view similar to FIG. 2 illustrating an optional construction for the present invention.
Figure 4:
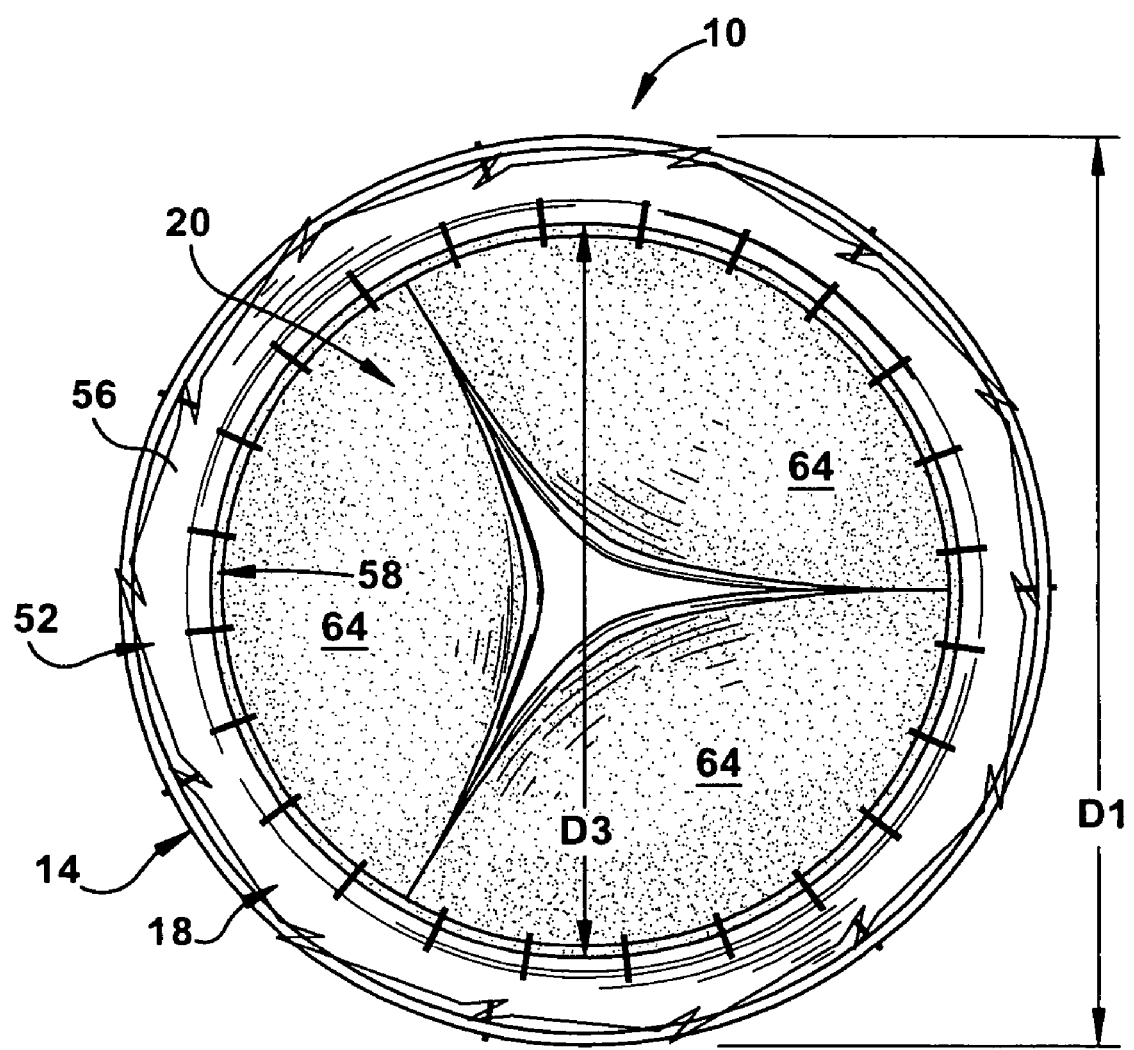
FIG. 4 is a sectional view taken along 4-4 in FIG. 3.

FIG. 5 illustrates an optional construction for the apparatus 10 in which an expandable ring 66 encircles the annulus 58 of the graft section 18 to support the prosthetic valve 20. The ring 66 may comprise a single wire or a small stent. The ring 66 may be made from a shape memory metal, such as Nitinol, or any other suitable medical grade plastic or metal. As shown in FIG. 5, the sutures that are used to secure the prosthetic valve 20 in the annulus 58 of the graft section 18 may extend around the ring 66 to strengthen the attachment of the valve 20 to the annulus of the graft section. Further, the ring 66 can be used to positively establish the third diameter D3 at the annulus 58 of the graft section 18.

Figure 6:
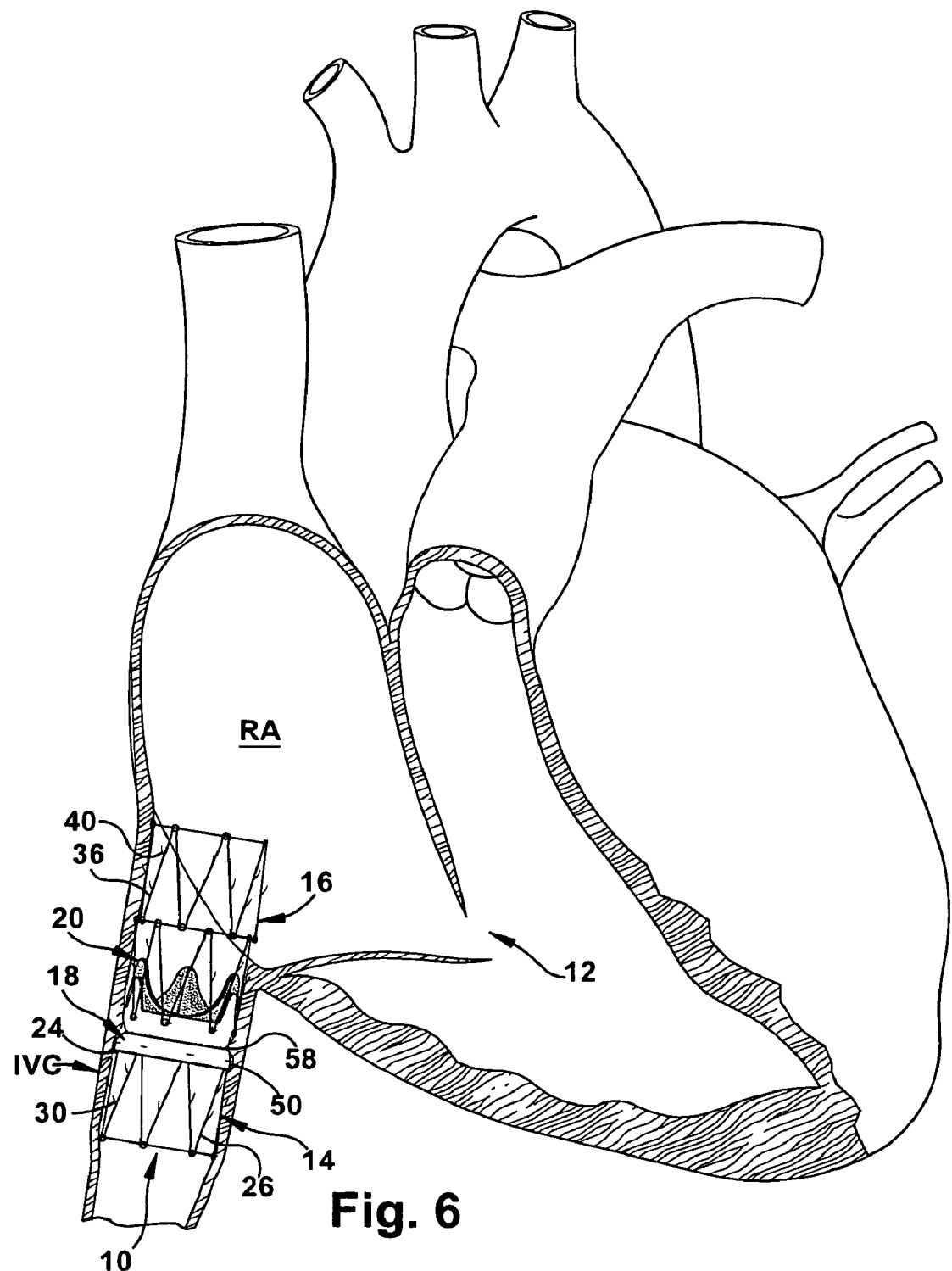
FIG. 6 is a schematic sectional view of a portion of a heart illustrating one option for placement of the apparatus of FIG. 1 to repair the function of a diseased tricuspid valve.

One application for the present invention is to repair the function of the diseased tricuspid valve 12 (FIG. 6). To enable delivery and deployment of the apparatus 10, the apparatus is radially collapsed and loaded into a sheath (not shown) over a catheter (not shown). After de-airing of the assembly, the apparatus 10 is delivered via a venotomy into the femoral vein and may be assisted with access through an internal jugular vein to establish through-and-through access. In the application of the apparatus 10 illustrated in FIG. 6, the apparatus is delivered to a desired location in the inferior vena cava (IVC) just below the right atrium (RA), but above the hepatic veins, under fluoroscopic and/or transesophageal echocardiographic guidance.

Once the apparatus 10 is advanced to the desired location, the sheath is retracted to allow the first and second support members 14 and 16 to expand radially outward into engagement with the IVC wall as shown in FIG. 6. It should be noted that a balloon (not shown) may be used to assist with the expansion or stabilization of one or both of the support members 14 and 16. As the support members 14 and 16 expand into the IVC wall, the hooks 30 and 40 on the beams 26 and 36 of the support members embed into the vessel wall to secure the apparatus 10 from migration in the IVC or right atrium.

Significantly, in the implanted condition shown in FIG. 6, the second support member 16 expands to the second diameter D2, which is the diameter of the IVC at that specific vascular location, and is able to independently expand and contract with the IVC in accordance with fluctuations in venous pressure or capacitance. Furthermore, the first support member 14 expands to the first diameter D1, which is the diameter of the IVC at that specific vascular location, and is able to independently expand and contract with the IVC in accordance with fluctuations in venous pressure or capacitance. In addition, the first end 50 of the graft section 18 that encircles the distal end 24 of the first support member 14 seals against the wall of the IVC to prevent any blood leakage around the apparatus 10.

Notwithstanding the flexibility of the diameters of the first and second support members 14 and 16, the diameter of the prosthetic valve 20 is predetermined by the third diameter D3 of the annulus 58 of the graft section 18 and is functionally independent of the diameters of the first and second support members. This functional independence of the diameter of the prosthetic valve 20 suspended within the graft section 18 helps to prevent antegrade and retrograde blood leaks around the prosthetic valve and ensures proper valvular function. Further, the extra-cardiac location of the apparatus 10 reduces potentially detrimental effects of cardiac contraction and provides an anatomically favorable region for fixation and sealing. Finally in the location shown in FIG. 6, the apparatus 10 eliminates systolic flow through the hepatic veins and IVC.

Figure 7:
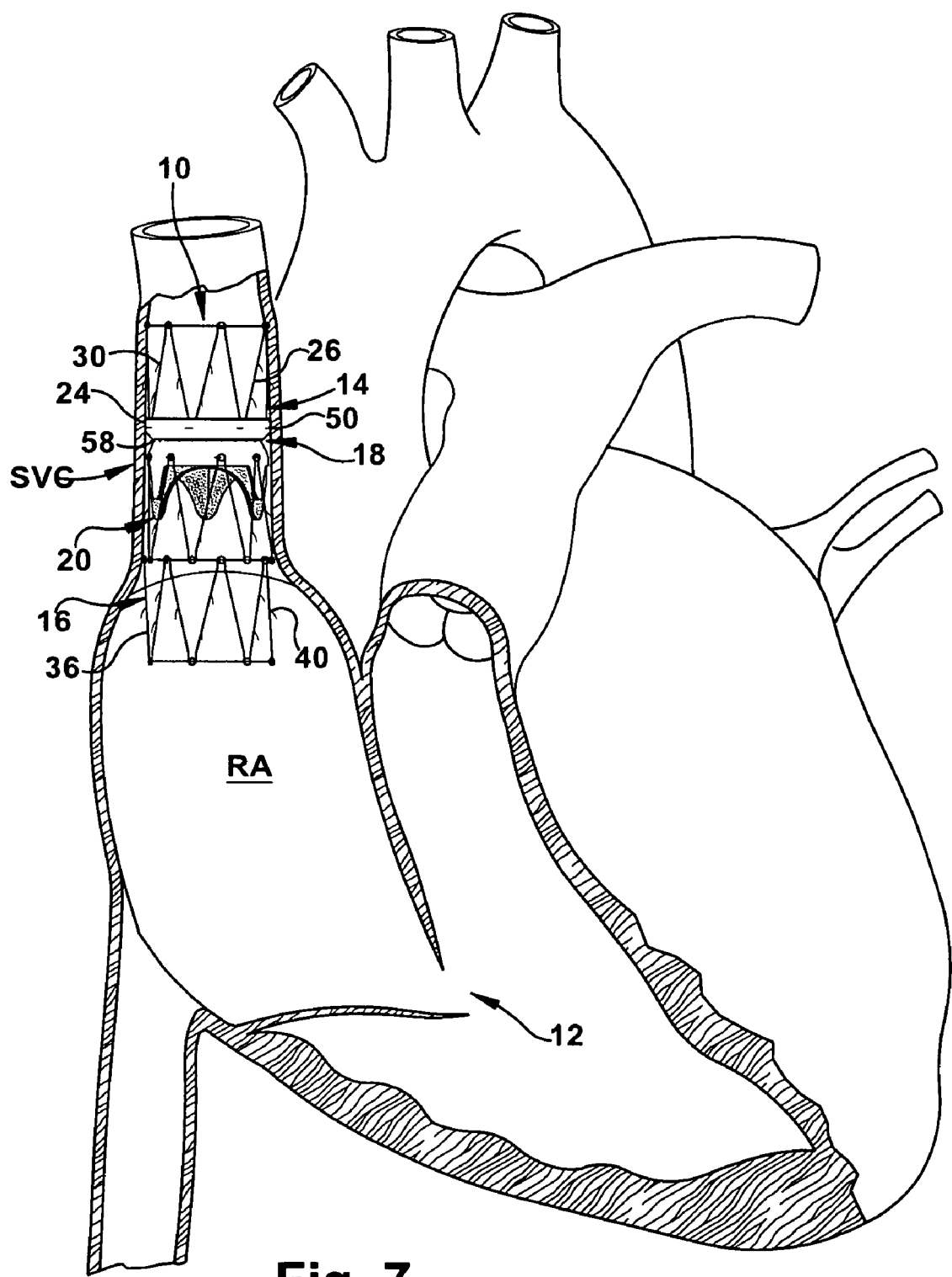
FIG. 7 is a view similar to FIG. 6 illustrating another option for placement of the apparatus of FIG. 1 to repair the function of a diseased tricuspid valve.

FIG. 7 illustrates placement of the apparatus 10 for repairing the function of the tricuspid valve in the superior vena cava (SVC). The apparatus 10 is delivered to a desired location in the SVC just above the right atrial junction, but below the azygos vein, under fluoroscopic and/or transesophageal echocardiographic guidance. The apparatus 10 is then deployed in the same basic manner as described above with regard to placement in the IVC.

In the implanted condition shown in FIG. 7, the second support member 16 expands to the second diameter D2, which is the diameter of the SVC at that specific vascular location, and is able to independently expand and contract with the SVC in accordance with fluctuations in venous pressure or capacitance. Furthermore, the first support member 14 expands to the first diameter D1, which is the diameter of the SVC at that specific vascular location, and is able to independently expand and contract with the SVC in accordance with fluctuations in venous pressure or capacitance. In addition, the first end 50 of the graft section 18 that encircles the distal end 24 of the first support member 14 seals against the wall of the SVC to prevent any blood leakage around the apparatus 10.

Notwithstanding the flexibility of the diameters of the first and second support members 14 and 16, the diameter of the prosthetic valve 20 is predetermined by the third diameter D3 of the annulus 58 of the graft section 18 and is functionally independent of the diameters of the first and second support members. This functional independence of the diameter of the prosthetic valve 20 suspended within the graft section 18 helps to prevent antegrade and retrograde blood leaks around the prosthetic valve and ensures proper valvular function.

Figure 8:
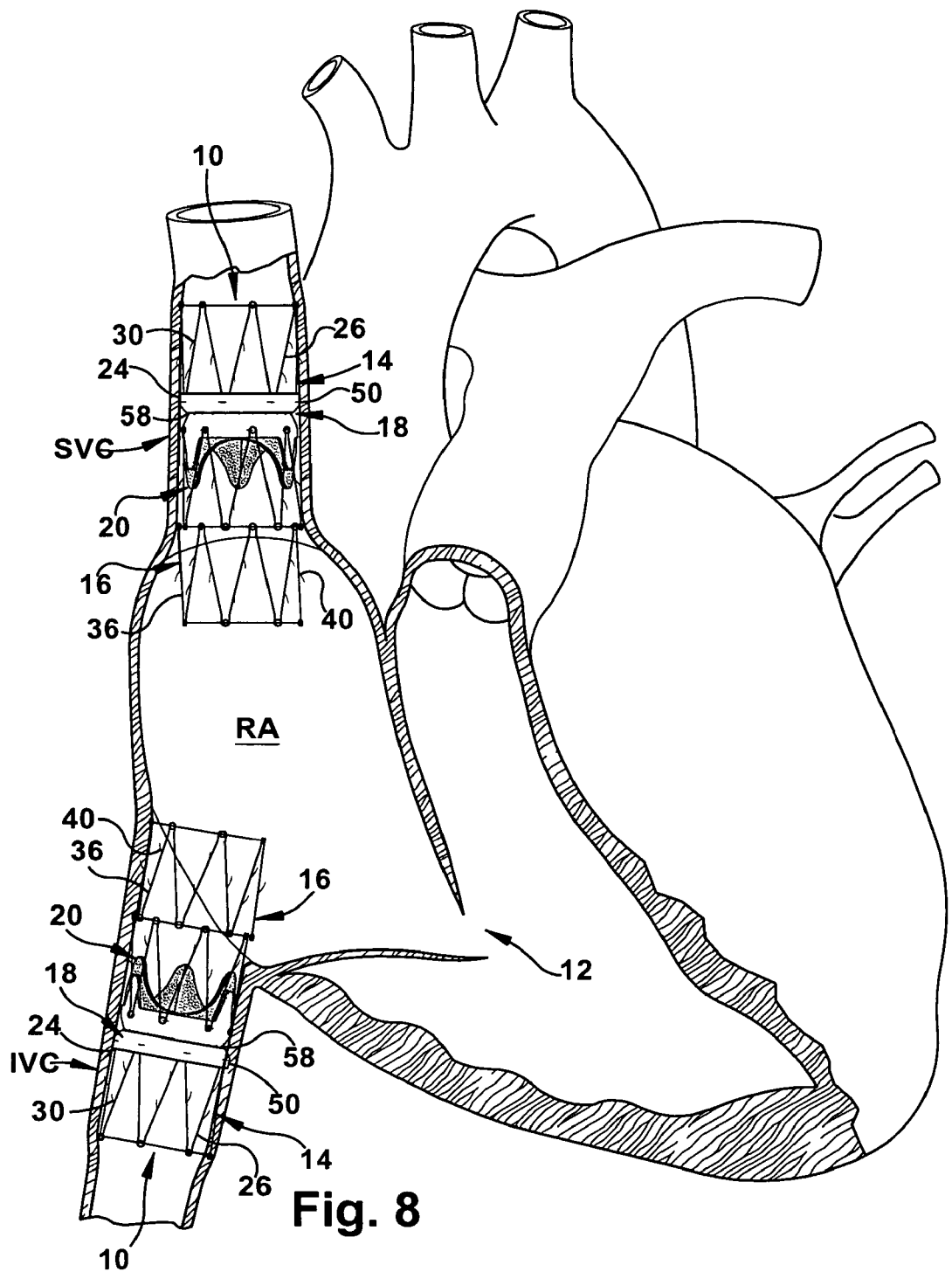
FIG. 8 is a view similar to FIGS. 6 and 7 illustrating yet another option for placement of the apparatus of FIG. 1 to repair the function of a diseased tricuspid valve.

FIG. 8 illustrates repairing the function of the tricuspid valve by placing a first apparatus 10 in the IVC and a second apparatus 10 in the SVC. The first apparatus 10 is placed in the IVC just below the right atrium but above the hepatic veins, and the second apparatus 10 is placed in the SVC just above the right atrial junction but below the azygos vein. Alternatively, it is contemplated that the apparatus may be formed by a single second support member 16 that spans from the SVC to the IVC.

Both the first apparatus 10 and the second apparatus 10 are deployed and function in the same basic manner as previously described. In the implanted condition shown in FIG. 8, the second support member 16 of the first apparatus 10 expands to the second diameter D2, which is the diameter of the IVC at that specific vascular location, and is able to independently expand and contract with the IVC in accordance with fluctuations in venous pressure or capacitance. Furthermore, the first support member 14 of the first apparatus 10 expands to the first diameter D1, which is the diameter of the IVC at that specific vascular location, and is able to independently expand and contract with the IVC in accordance with fluctuations in venous pressure or capacitance. In addition, the first end 50 of the graft section 18 of the first apparatus 10 that encircles the distal end 24 of the first support member 14 seals against the wall of the IVC to prevent any blood leakage around the apparatus.

Similarly, the second support member 16 of the second apparatus 10 expands to the second diameter D2, which is the diameter of the SVC at that specific vascular location, and is able to independently expand and contract with the SVC in accordance with fluctuations in venous pressure or capacitance. Furthermore, the first support member 14 of the second apparatus 10 expands to the first diameter D1, which is the diameter of the SVC at that specific vascular location, and is able to independently expand and contract with the SVC in accordance with fluctuations in venous pressure or capacitance. In addition, the first end 50 of the graft section 18 of the second apparatus 10 that encircles the distal end 24 of the first support member 14 seals against the wall of the SVC to prevent any blood leakage around the apparatus.

Notwithstanding the flexibility of the diameters of the first and second support members 14 and 16 of each apparatus 10, the diameter D3 of each of the prosthetic valves 20 is predetermined by the third diameter D3 of the annulus 58 of the respective graft section 18 and is functionally independent of the diameters of the first and second support members. This functional independence of the diameter of each of the prosthetic valves 20 helps to prevent antegrade and retrograde blood leaks around the prosthetic valves and ensures proper valvular function.

Figure 9:
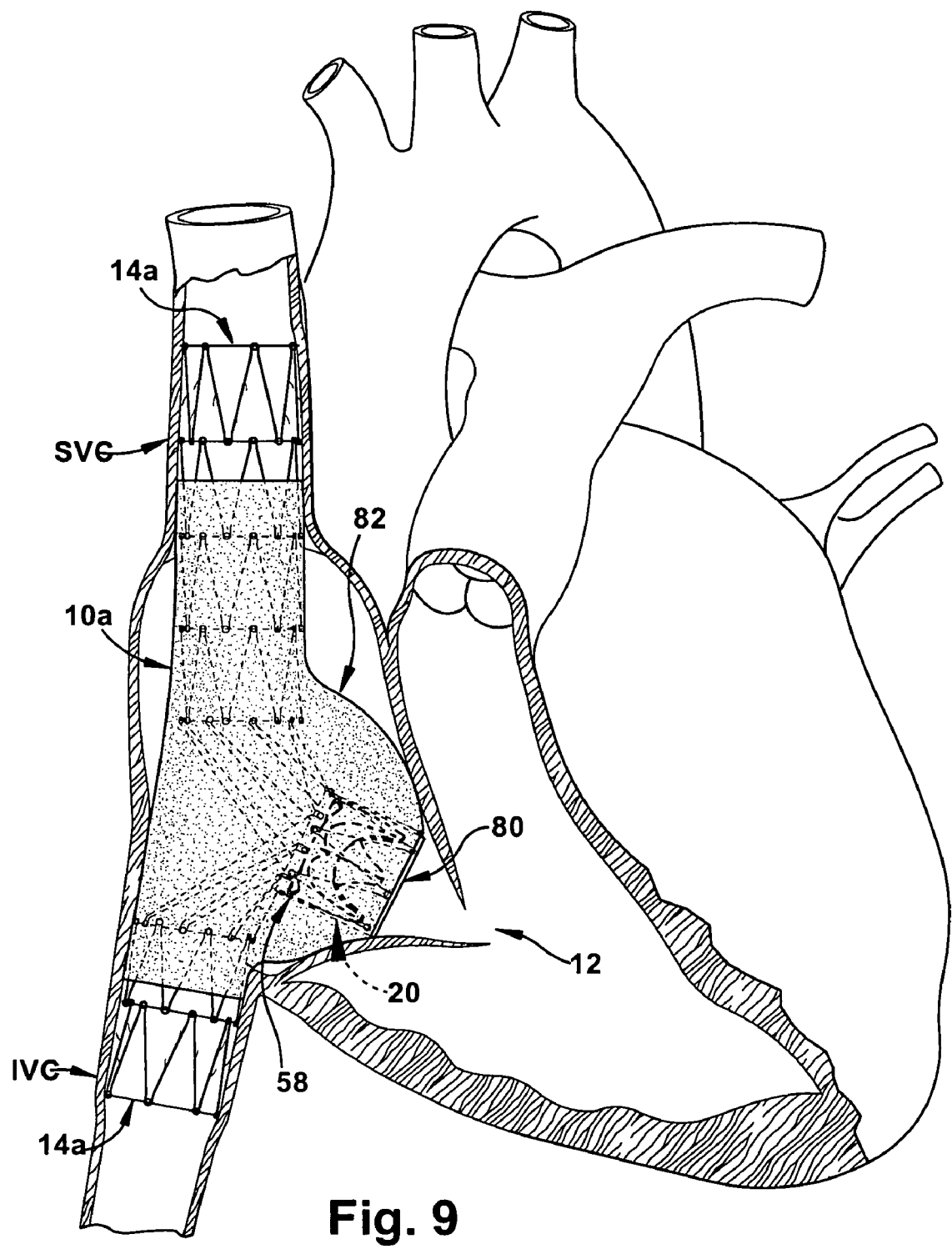
FIG. 9 is a view similar to FIGS. 6-8 illustrating still another option for placement of the apparatus of FIG. 1 to repair the function of a diseased tricuspid valve.

FIG. 9 illustrates another option for repairing the function of the diseased tricuspid valve 12 using a modified version of the apparatus. In FIG. 9, components of the apparatus that are similar, but not identical, to previously described components carry the suffix "a". The apparatus 10a includes lower and upper support sections 14a, a valve section 80 suspended between the support sections, and a graft enclosure 82.

The lower support section 14a of the apparatus 10a is placed in the IVC just below the right atrium but above the hepatic veins, and the upper support section 14a is placed in the SVC just above the right atrial junction but below the azygos vein. The valve section 80 includes a support member 16a and the bioprosthetic valve 20 secured therein. The valve section 80 is deployed in the right atrium at a location adjacent the tricuspid valve 12. The graft enclosure 82 extends over the valve section 80 and the majority of the lower and upper support sections 14a to form a lining in the right atrium between the valve section, the IVC, and the SVC.

In the implanted condition shown in FIG. 9, the lower support section 14a expands to the diameter of the IVC and is able to independently expand and contract with the IVC in accordance with fluctuations in venous pressure or capacitance. In addition, the portion of the graft enclosure 82 that covers the lower support section 14a seals against the wall of the IVC to prevent any blood leakage around the apparatus 10a. Similarly, the upper support section 14a expands to the diameter of the SVC and is able to independently expand and contract with the SVC in accordance with fluctuations in venous pressure or capacitance. The portion of the graft enclosure 82 that covers the upper support section 14a seals against the wall of the SVC to prevent any blood leakage around the apparatus 10a.

Notwithstanding the flexibility of the diameters of the lower and upper support sections 14a, the diameter of the prosthetic valve 20 is predetermined by the third diameter D3 of the annulus 58 of the valve section 80 and is functionally independent of the diameters of the support sections.

The apparatus 10 and 10a and associated methods described above help to protect the lower and/or upper body from elevated venous pressures caused by a diseased tricuspid valve. Problems such as ascites, liver dysfunction, edema and cardiac cirrhosis that are often associated with severe tricuspid valve regurgitation can be treated using the apparatus and methods according to the present invention. Further, the apparatus 10 and 10a and methods of the present invention provide a minimally invasive, endovascular approach to treat severe valvular disease, which is particularly important for high risk patients.

Figure 10:
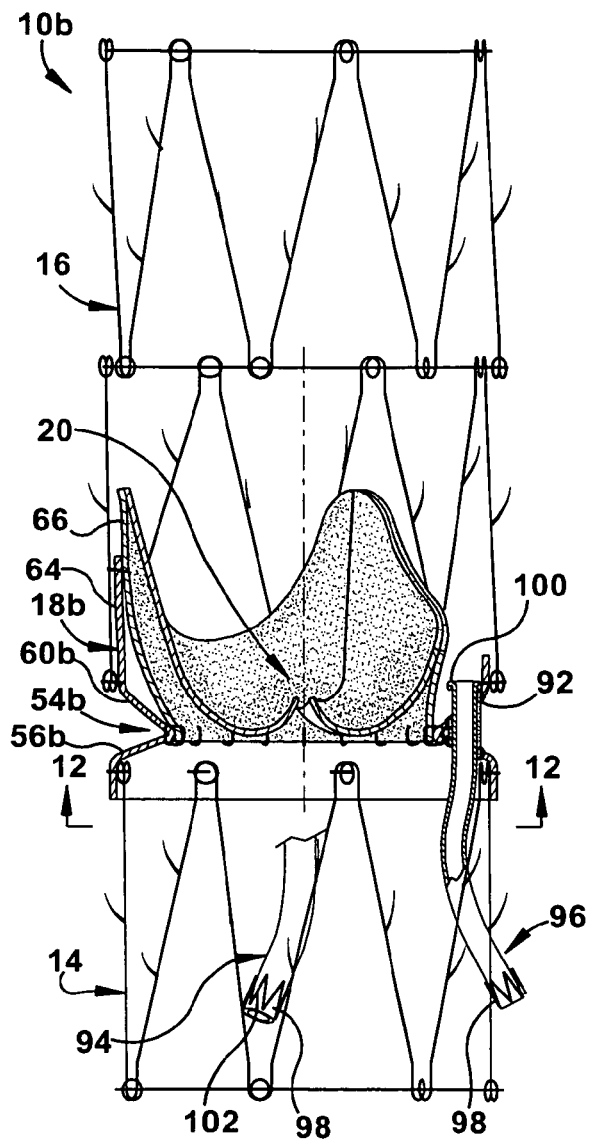
FIG. 10 is a schematic sectional view of an apparatus for repairing the function of a diseased valve in accordance with a second embodiment of the present invention.
Figure 11:
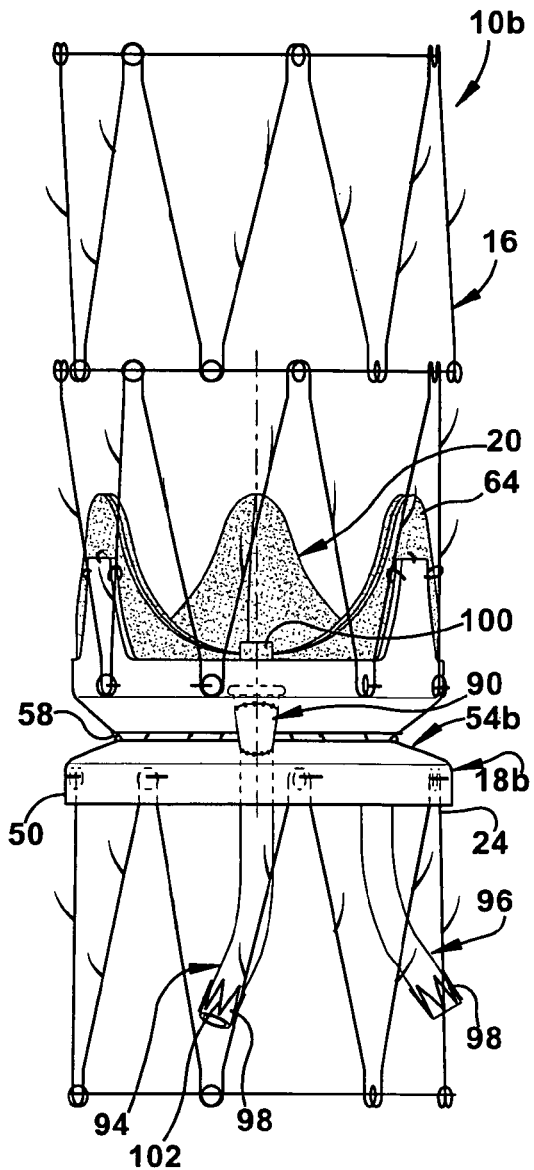
FIG. 11 is a schematic side view of the apparatus of FIG. 10.
Figure 12:
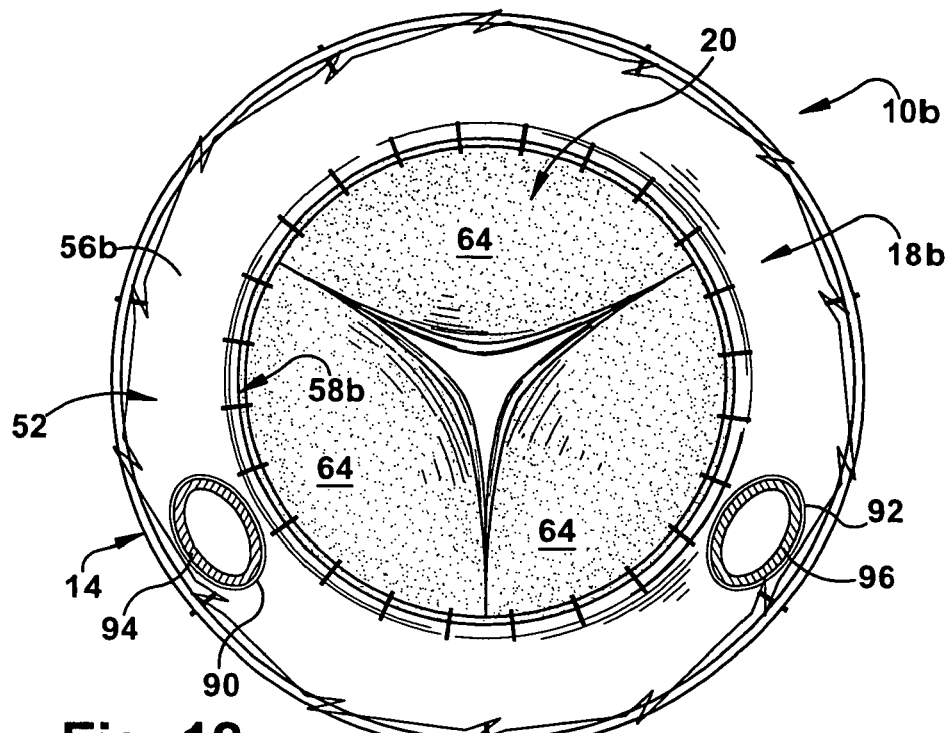
FIG. 12 is a sectional view taken along 12-12 in FIG. 10.

FIGS. 10-12 illustrate an apparatus for repairing the function of a diseased valve in accordance with a second embodiment of the present invention. In the second embodiment of FIGS. 10-12, components of the apparatus that are similar, but not identical, to previously described components carry the suffix "b".

The graft section 18b of the apparatus 10b includes first and second passages 90 and 92 extending axially through the neck portion 54b. Each of the first and second passages 90 and 92 terminates at openings in the converging portion 56b and the diverging portion 60b, respectively. As shown in FIG. 12, the passages 90 and 92 are spaced circumferentially apart and may have an elliptical shape in cross-section. It should be understood that the spacing and quantity of passages 90 and 92 may be varied based on the specific application for the apparatus 10b. The apparatus 10b of FIGS. 10-12 is configured for repairing the function of a diseased aortic or other type of valve (not shown).

The apparatus 10b further includes first and second tubular conduits 94 and 96 that are receivable in the first and second passages 90 and 92, respectively. The first and second conduits 94 and 96 are made of a biocompatible material such as Dacron®, woven velour, polyurethane, PTFE, or heparin-coated fabric. Alternatively, the conduits 94 and 96 may be made from a biological material such as bovine or equine pericardium, a homograft, an autograft, or cell-seeded tissue. It should be understood that the quantity of conduits 94 and 96 may be varied based on the specific application for the apparatus 10b.

Each of the first and second conduits 94 and 96 has oppositely disposed first and second ends 98 and 100. The first end 98 of each of the conduits 94 and 96 may have a cylindrical configuration supported by a stent 102 for securing the first end in a branch vessel. The second end 100 of each of the conduits 94 and 96 may have an elliptical configuration for mating with the elliptical passages 90 and 92. The second end 100 of the conduits 94 and 96 will be larger in diameter than the first end 98 so that the conduits taper in diameter from the second end to the first end. This taper assists in inserting the conduits 94 and 96 into the passages 90 and 96 and in ensuring a sealed connection between the conduits and the graft section 18b. As shown in FIG. 11, it is contemplated that the Nitinol ring 66, previously described with regard to FIG. 5, could also be used in the embodiment of FIGS. 10-12.

Figure 13:
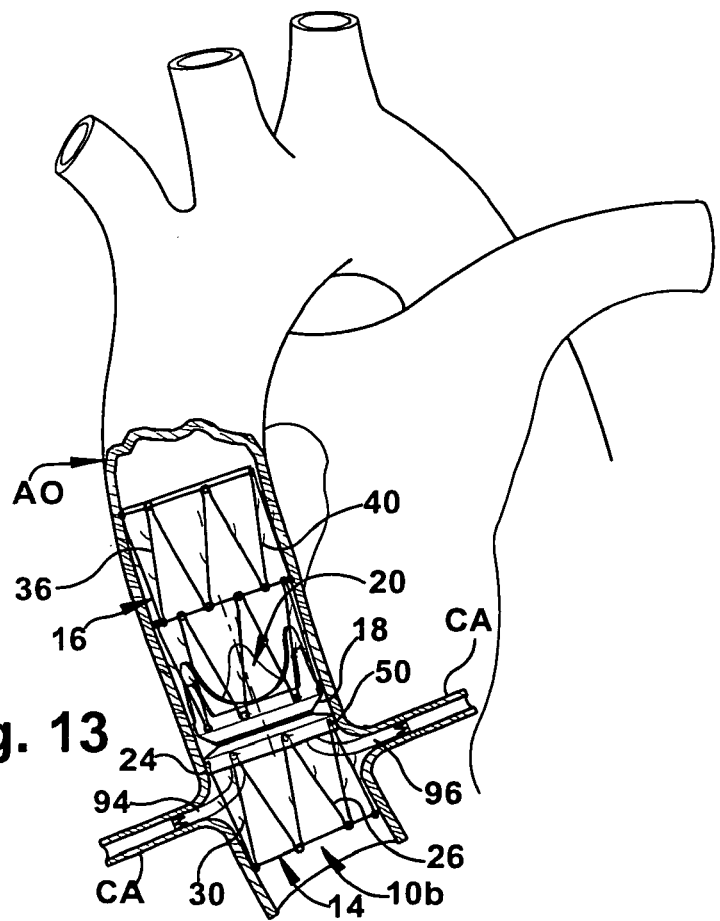
FIG. 13 is a schematic sectional view of a portion of a heart illustrating one option for placement of the apparatus of FIG. 10 to repair the function of a diseased aortic valve.

FIG. 13 illustrates placement of the apparatus 10b in accordance with the second embodiment to repair the function of a diseased aortic valve. It should be noted that it may be desirable to excise the native aortic leaflets prior to implantation of the apparatus 10b. To enable delivery and deployment of the apparatus, the apparatus 10b is radially collapsed and loaded into a sheath (not shown) over a catheter (not shown). Carotid or subclavian access may be used to cannulate the aorta (AO) and each of the two coronary arteries (CA).

After de-airing of the assembly, the apparatus 10b is introduced into the aorta. Under fluoroscopic and/or transesophageal echocardiographic guidance, the apparatus 10b is advanced to the desired location above the annulus of the native aortic valve. Wires placed within the coronary arteries may be loaded through guides (not shown) in the conduits 94 and 96 to ensure proper orientation. The sheath is retracted to allow the first and second support members 14 and 16 to expand radially outward into engagement with the aortic wall as shown in FIG. 13. It should be noted that a balloon (not shown) may be used to assist with the expansion of one or both of the support members 14 and 16. As the support members 14 and 16 expand into the vessel wall, the hooks 30 and 40 on the beams 26 and 36 of the support members embed into the vessel wall to secure the apparatus 10b from migration in the aorta.

The first and second conduits 94 and 96 are then inserted into the passages 90 and 92 in the graft section 18b and the first end 98 of each of the conduits is placed into the coronary arteries. The placement of the conduits 94 and 96 into the coronary arteries bridges the prosthetic valve 20 with the conduits and allows the arteries to be perfused during diastole, or systole (depending on the valve structure).

In the implanted condition shown in FIG. 13, the second support member 16 expands to the second diameter D2, which is the diameter of the ascending aortic, and is able to independently expand and contract with the aorta in accordance with fluctuations in venous pressure or capacitance. Furthermore, the first support member 14 expands to the first diameter D1, which is the diameter of the aortic root, and is able to independently expand and contract with the aorta in accordance with fluctuations in venous pressure or capacitance. In addition, the first end 50 of the graft section 18b that encircles the distal end 24 of the first support member 14 seals against the wall of the aorta to prevent any blood leakage around the apparatus 10b.

Notwithstanding the flexibility of the diameters of the first and second support members 14 and 16, the diameter of the prosthetic valve 20 is predetermined by the third diameter D3 of the annulus 58 of the graft section 18b and is functionally independent of the diameters of the first and second support members. This functional independence of the diameter of the prosthetic valve 20 suspended within the graft section 18b helps to prevent antegrade and retrograde blood leaks around the prosthetic valve and ensures proper valvular function.

Figure 14:
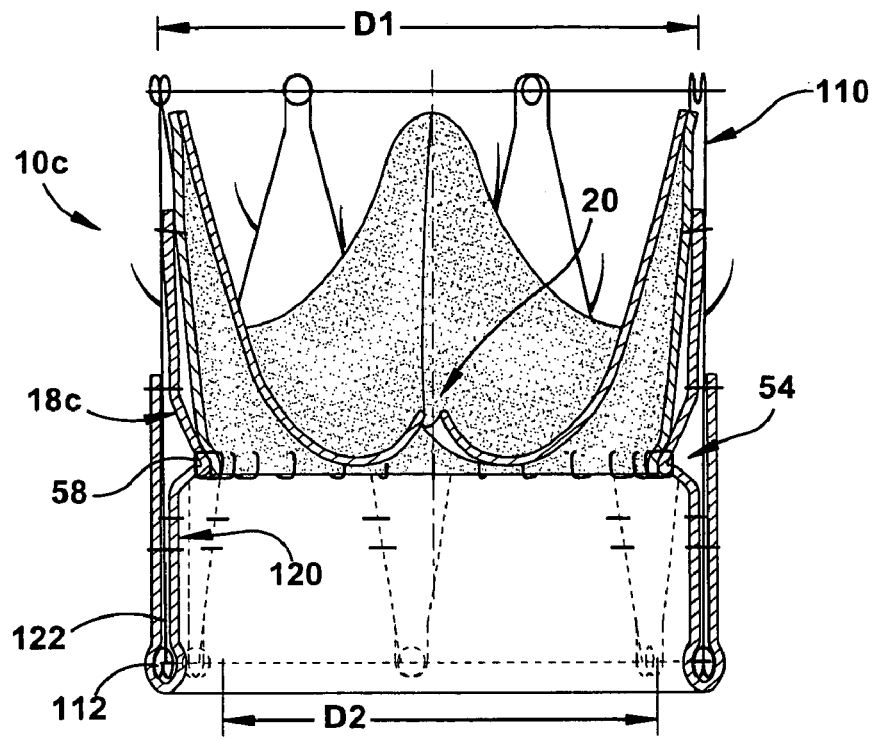
FIG. 14 is a schematic sectional view of an apparatus for repairing the function of a diseased valve in accordance with a third embodiment of the present invention.

FIG. 14 illustrates an apparatus for repairing the function of a diseased valve in accordance with a third embodiment of the present invention. In the third embodiment of FIG. 14, components of the apparatus that are similar, but not identical, to previously described components carry the suffix "c".

The primary difference between the apparatus 10c of FIG. 14 and the apparatus of FIGS. 1-4 is the use of a single support member 110 that is expandable to a first diameter D1. A first graft section 120 is secured to the inner surface of the support member 110. The prosthetic valve 20 is suspended within the annulus 58 of the neck portion 54 of the graft section 120 at a second diameter D2 that is smaller than and independent of the first diameter D1 of the support member. A second graft section 122 extends from the first graft section 120 and wraps around a first end 112 of the support member 110, although it should be understood that the first and second graft sections could be made of separate pieces of material. It is contemplated that the Nitinol ring 66, previously described with regard to FIG. 5, could also be used in the embodiment of FIG. 14.

The apparatus 10c may be deployed in the same basic manner as described above with regard to the other embodiments to repair the function of a diseased tricuspid valve. Once implanted in either the SCV or the IVC, the support member 110 expands to the first diameter D1, which is the diameter of the vasculature at that specific location, and is able to independently expand and contract with the vasculature in accordance with fluctuations in venous pressure or capacitance. In addition, the second graft section 122 that encircles the first end 112 of the support member 110 seals against the wall of the vasculature to prevent any blood leakage around the apparatus 10$c$.

Notwithstanding the flexibility of the first diameter D1 of the support member 110, the diameter of the prosthetic valve 20 is predetermined by the second diameter D2 of the annulus 58 of the graft section 120 and is functionally independent of the diameter of the support member. This functional independence of the diameter of the prosthetic valve 20 suspended within the graft section 120 helps to prevent antegrade and retrograde blood leaks around the prosthetic valve and ensures proper valvular function.

Figure 15:
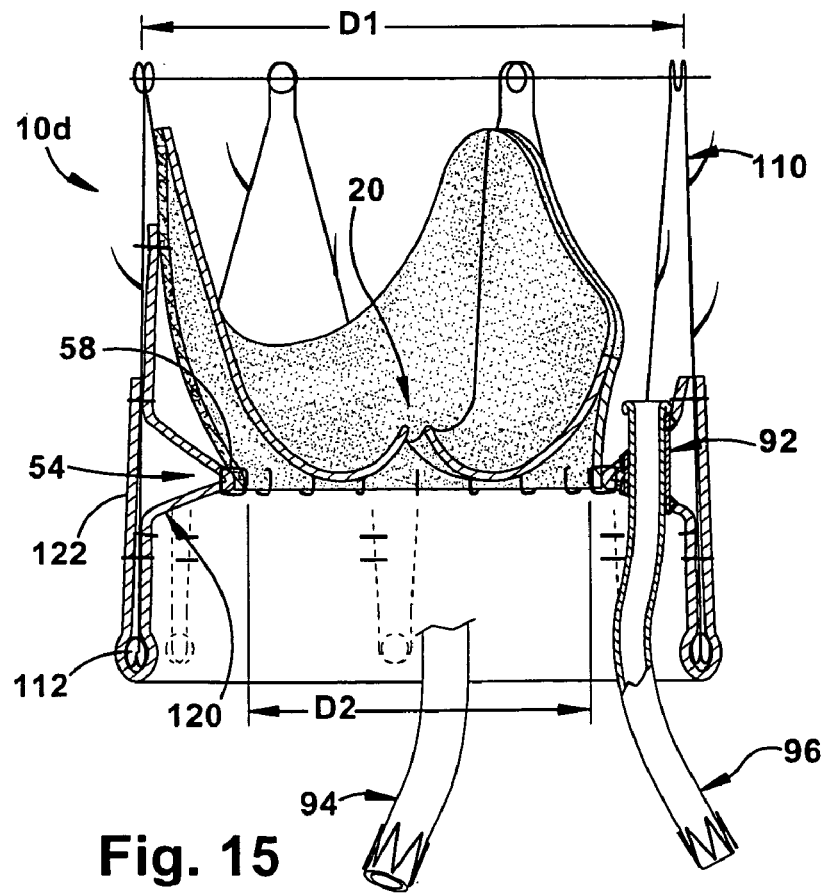
FIG. 15 is a schematic sectional view of an apparatus for repairing the function of a diseased valve in accordance with a fourth embodiment of the present invention.

FIG. 15 illustrates an apparatus for repairing the function of a diseased valve in accordance with a fourth embodiment of the present invention. In the fourth embodiment of FIG. 15, components of the apparatus that are similar, but not identical, to previously described components carry the suffix "d". The apparatus 10$d$ of FIG. 15 is similar to the apparatus of FIG. 14, but includes the first and second passages 90 and 92 and corresponding first and second tubular conduits 94 and 96 of FIGS. 10-12 so that the apparatus can be used to repair the function of a diseased aortic valve. The first and second conduits 94 and 96 are inserted into the passages 90 and 92 in the graft section 120 following placement of the apparatus 10$d$ above the native aortic valve, and the first end 98 of each of the conduits is placed into the coronary arteries. The placement of the conduits 94 and 96 into the coronary arteries allows the arteries to be perfused during diastole.

When implanted, the support member 110 expands to the first diameter D1, which is the diameter of the aorta at that specific location, and is able to independently expand and contract with the aorta in accordance with fluctuations in venous pressure or capacitance. In addition, the second graft section 122 that encircles the first end 112 of the support member 110 seals against the wall of the aorta to prevent any blood leakage around the apparatus.

Notwithstanding the flexibility of the first diameter D1 of the support member 110, the diameter of the prosthetic valve 20 is predetermined by the second diameter of the annulus 58 of the graft section 120 and is functionally independent of the diameter of the support member. This functional independence of the diameter of the prosthetic valve 20 suspended within the graft section 120 helps to prevent antegrade and retrograde blood leaks around the prosthetic valve and ensures proper valvular function.

FIGS. 16-17 illustrate an apparatus 10$e$ for repairing the function of a diseased valve in accordance with a fifth embodiment of the present invention. In the fifth embodiment of FIGS. 16-17, components of the apparatus that are similar, but not identical, to previously described components carry the suffix "e". Description of common elements and operation similar to those in the previously described embodiments will not be repeated with respect to the fifth embodiment.

The primary difference between the apparatus 10$e$ of FIGS. 16-17 and the apparatus 10 of FIGS. 1-4 is that the second end portion 52 of the graft section 18 further includes a plurality of extension stents 62$e$ that extend axially toward the distal end 34 of the second support member 16, in lieu of the extension flaps 62 of the previously described apparatus 10. The extension stents 62$e$ are each connected, such as by sutures, to one of the leaflets 64 of the bioprosthetic valve 20 and may act to support the leaflets 64 in a desired manner. The number and circumferential orientation of the extension stents 62$e$ should correspond to the number and orientation of leaflets 64 in the bioprosthetic valve 20. It is contemplated that the Nitinol ring 66, previously described with regard to FIG. 5, could also be used in the fifth embodiment of FIGS. 16-17 to anchor the extension stents 62$e$. Conversely, the extension stents 62$e$ could be directly anchored, via sutures or the like, to the second end portion 52 of the graft section 18, as shown in FIGS. 16-17.

FIGS. 18-19 illustrate an apparatus for repairing the function of a diseased valve in accordance with a sixth embodiment of the present invention. In the sixth embodiment of FIGS. 18-19, components of the apparatus that are similar, but not identical, to previously described components carry the suffix "f". Description of common elements and operation similar to those in the previously described embodiments will not be repeated with respect to the sixth embodiment.

The primary difference between the apparatus 10$f$ of FIGS. 18-19 and the apparatus 10$e$ of FIGS. 16-17 is that the plurality of extension stents 62$f$, extending axially toward the distal end 34 of the second support member 16, are connected together at a distal end (not numbered) thereof by a stent ring 124. The extension stents 62$f$ are each connected, such as by sutures, to one of the leaflets 64 of the bioprosthetic valve 20 and to the stent ring 124. The extension stents 62$f$ may act to support the leaflets 64 in a desired manner in cooperation with the stent ring 124. As in the aforementioned embodiments, the number and circumferential orientation of the extension stents 62$f$ of the sixth embodiment should correspond to the number and orientation of leaflets 64 in the bioprosthetic valve 20.

Figure 20:
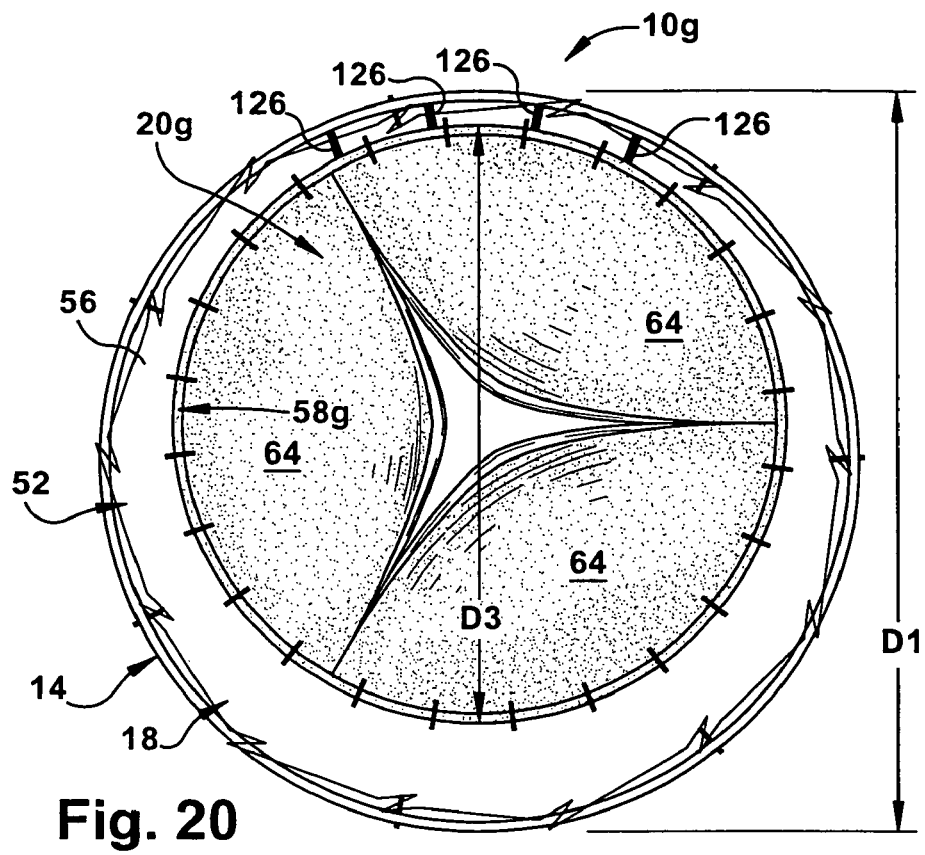
FIG. 20 is a sectional view of an apparatus for repairing the function of a diseased valve in accordance with a seventh embodiment of the present invention.

FIG. 20 illustrates an apparatus for repairing the function of a diseased valve in accordance with a seventh embodiment of the present invention. In the seventh embodiment of FIG. 20, components of the apparatus that are similar, but not identical, to previously described components carry the suffix "g". Description of common elements and operation similar to those in the previously described embodiments will not be repeated with respect to the seventh embodiment.

The primary difference between the apparatus 10$g$ of FIG. 20 and the apparatus 10 of FIGS. 1-4 is that the bioprosthetic valve 20$g$ is secured, by sutures or other suitable means, in an off-center orientation within a cross-section of the graft section 18, as shown in FIG. 20. One or more biasing sutures 126 is placed to draw the annulus 58$g$ of the neck portion 54$g$ of the graft section 18, to which the bioprosthetic valve 20$g$ is secured, toward a chosen side of the annular first or second support member 14 or 16. This off-center placement of the bioprosthetic valve 20$g$ with respect to the graft section 18, as seen in cross-section, allows the apparatus 10$g$ to have a desired directionality. The directionality, or radial orientation, of the off-center bioprosthetic valve 20$g$ of the apparatus 10$g$ according to the seventh embodiment may be readily selected by one of ordinary skill in the art for a particular application of the present invention.

Figure 21:
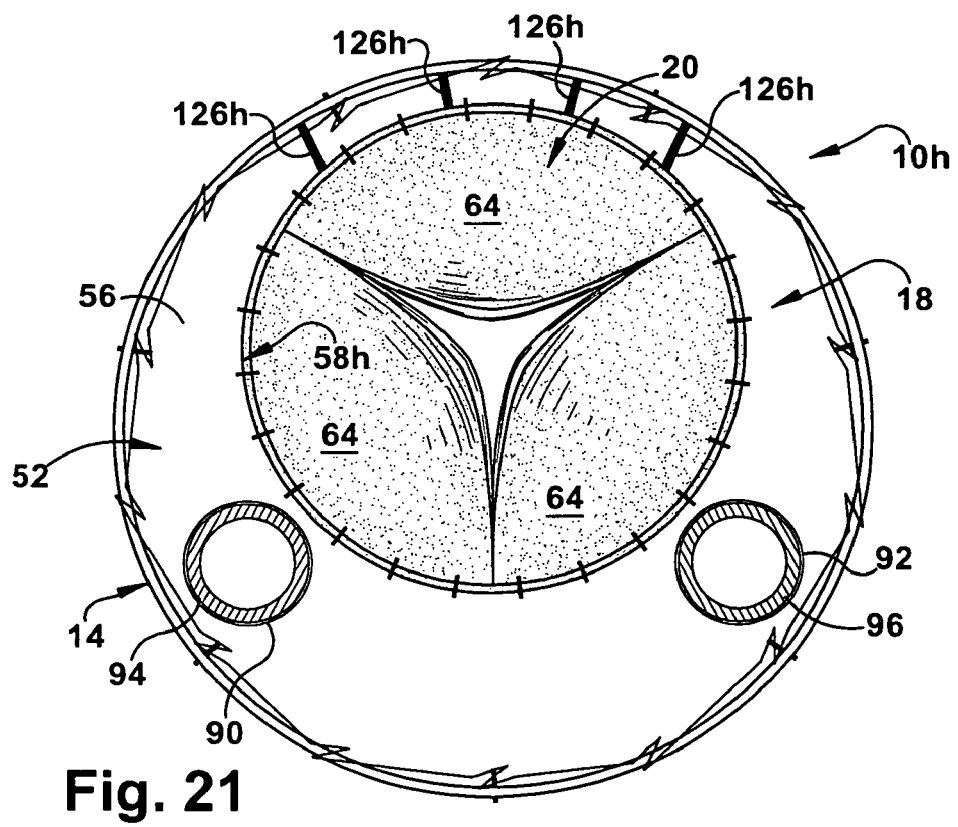
FIG. 21 is a sectional view of an apparatus for repairing the function of a diseased valve in accordance with an eighth embodiment of the present invention.

FIG. 21 illustrates an apparatus for repairing the function of a diseased valve in accordance with an eighth embodiment of the present invention. In the eighth embodiment of FIG. 21, components of the apparatus that are similar, but not identical, to previously described components carry the suffix "h". Description of common elements and operation similar to those in the previously described embodiments will not be repeated with respect to the eighth embodiment.

The primary difference between the apparatus 10$h$ of FIG. 21 and the apparatus 10$b$ of FIGS. 10-12 is that the bioprosthetic valve 20h is secured, by sutures or other suitable means, in an off-center orientation within a cross-section of the graft section 18, as shown in FIG. 21 and in a similar manner to the apparatus 10g of the seventh embodiment. One or more biasing sutures 126 is placed to draw the annulus 58h of the neck portion 54 of the graft section 18, to which the bioprosthetic valve 20h is secured, toward a chosen side of the annular first or second support member 14 or 16. This off-center placement of the bioprosthetic valve 20h with respect to the graft section 18, as seen in cross-section, allows the apparatus 10h to have a desired directionality. The directionality, or radial orientation, of the off-center bioprosthetic valve 20h of the apparatus 10h according to the eighth embodiment may be readily selected by one of ordinary skill in the art for a particular application of the present invention. For example, the directionality of the off-center bioprosthetic valve 20h may be chosen to bias the bioprosthetic valve 20h away from the first and second conduits 94 and 96, as shown in FIG. 21, and thereby avoid crushing or other fluid obstruction of the first and second conduits.

From the above description of the invention, those skilled in the art will perceive improvements, changes and modifications. As mentioned previously, it should be understood by those skilled in the art that the apparatus and methods disclosed above could be adapted for repairing the function of a venous valve. Such improvements, changes and modifications within the skill of the art are intended to be covered by the appended claims.

Having described the invention, I claim:

1. An apparatus for repairing the function of a diseased valve, the apparatus comprising:

a tubular first support member expandable to a first diameter and having oppositely disposed proximal and distal first support member ends;

a tubular second support member spaced axially apart from the first support member and expandable to a second diameter that is independent of the first diameter, the second support member having oppositely disposed proximal and distal second support member ends;

a tubular graft section interconnecting the first and second support members and defining an annulus having a third diameter that is independent of each of the first and second diameters, the graft section having oppositely disposed proximal and distal graft section ends, the proximal graft section end being connected directly to the distal first support member end and the distal graft section end being connected directly to the proximal second support member end; and a prosthetic valve secured within the annulus of the graft section, the prosthetic valve having at least two valve leaflets that are coaptable to permit the unidirectional flow of blood; wherein the first and second support members are interconnected only by the graft section, and the prosthetic valve is directly secured only to the graft section; and wherein the graft section has an hourglass shape with a neck portion, the neck portion of the graft section defining the annulus of the valve, and a converging portion and a diverging portion on opposite sides of the neck portion; and at least one conduit puncturing longitudinally through the converging and diverging neck portions and connecting to form a smaller secondary lumen therethrough.

2. The apparatus of claim 1, further comprising an expandable ring encircling the annulus of the graft section and supporting the prosthetic valve secured within the annulus.

3. The apparatus of claim 1, wherein the graft section overlaps and is secured to an outer surface of at least one of the first and second support members.

4. The apparatus of claim 1, wherein the graft section overlaps and is secured to an outer surface of one of the first and second support members and the graft section overlaps and is secured to an inner surface of the other of the first and second support members.

5. The apparatus of claim 1, further comprising at least one tubular conduit having first and second ends, the second end being received in the at least one passage in the graft section, the first end for positioning in a branch blood vessel.

6. The apparatus of claim 1, further comprising at least two graft extensions having first and second ends, the first end of each graft extension being secured to the graft section and the second end of each graft extension providing support to a valve leaflet.

7. The apparatus of claim 6, wherein each graft extension is formed integrally with the graft section.

8. The apparatus of claim 6, further comprising an extension support ring, with the second end of each graft extension being attached to the extension support ring.

9. The apparatus of claim 1, wherein the prosthetic valve has a center valve axis, the graft section has a center graft axis, and the prosthetic valve is secured within the annulus of the graft section with the center valve axis being axially offset from the center graft axis.

10. The apparatus of claim 1, wherein the first and second support members are each substantially made from a first material and the graft section is substantially made from a second material.

\* \* \* \* \*